United States Patent
Deschler et al.

(10) Patent No.: US 10,466,035 B2
(45) Date of Patent: Nov. 5, 2019

(54) COMBINATION SENSOR

(71) Applicant: SCHLEUNIGER HOLDING AG, Thun (CH)

(72) Inventors: Raphael Deschler, Oberhofen (CH); Michael Jost, Thun (CH); Christian Huggler, Steffisburg (CH); Reto Hofer, Faulensee (CH)

(73) Assignee: SCHLEUNIGER HOLDING AG, Thun (CH)

( * ) Notice: Subject to any disclaimer, the term of this patent is extended or adjusted under 35 U.S.C. 154(b) by 0 days.

(21) Appl. No.: 16/089,714

(22) PCT Filed: Mar. 31, 2017

(86) PCT No.: PCT/IB2017/000355
§ 371 (c)(1),
(2) Date: Sep. 28, 2018

(87) PCT Pub. No.: WO2017/168236
PCT Pub. Date: Oct. 5, 2017

(65) Prior Publication Data
US 2019/0113330 A1 Apr. 18, 2019

(30) Foreign Application Priority Data
Apr. 1, 2016 (EP) .................................... 16163595

(51) Int. Cl.
*G01B 11/10* (2006.01)
*G01B 7/02* (2006.01)
(Continued)

(52) U.S. Cl.
CPC .............. *G01B 11/10* (2013.01); *G01B 7/023* (2013.01); *G01B 7/12* (2013.01); *G01B 7/125* (2013.01);
(Continued)

(58) Field of Classification Search
CPC ........... G01N 21/8915; G01N 21/8983; G01N 33/365; G01N 21/89; G01N 21/94;
(Continued)

(56) References Cited

U.S. PATENT DOCUMENTS 6,201,602 B1 * 3/2001 Bouvyn ............. G01N 21/8915
356/238.1
6,449,345 B1 9/2002 Grimes
(Continued)

FOREIGN PATENT DOCUMENTS

CN 87214470 U 5/1988
CN 1403821 A 3/2003
(Continued)

OTHER PUBLICATIONS

International Search Corresponding to PCT/IB2017/000355 dated Jun. 26, 2017.
(Continued)

*Primary Examiner* — Michael P Stafira
(74) *Attorney, Agent, or Firm* — Davis & Bujold PLLC; Michael J. Bujold (57) ABSTRACT

An arrangement for automatically contactlessly detecting elongate objects (W), such as cables, wires or profiles, has a quasi-coaxially arranged group of a first optical measuring system (D) for determining the external diameter and a second optical measuring system (C) for determining the color using a different measurement principle. The functional and local separation of the two measuring systems (C, D) is achieved by using different wavelength ranges and by a long-pass filter (C3). A third, virtual measuring system (P) may be provided for the purpose of determining the cable location and is used to weight measured values of the color measurement and measured values of an optional eddy current sensor. The optical measuring systems (D, C, P) for
(Continued)

determining the diameter, the color and the position have a common optical disc-shaped measuring volume (DCPv) which is preferably arranged centrally in the guide device (4a, 4b) for the elongate object (W).

18 Claims, 7 Drawing Sheets

(51) Int. Cl.
    *G01B 7/12*     (2006.01)
    *G01B 11/08*     (2006.01)
    *G01N 21/952*     (2006.01)
    *G01J 3/50*     (2006.01)

(52) U.S. Cl.
    CPC .............. *G01B 11/08* (2013.01); *G01J 3/501* (2013.01); *G01N 21/952* (2013.01)

(58) Field of Classification Search
CPC .... G01N 21/898; G01N 21/88; G01N 21/952; G01N 33/367; G01N 2021/8472; G01N 2021/945; G01N 21/47; G01N 21/86; G01N 21/8806; G01N 21/8903; G01N 21/95; G01N 33/34; G01N 15/0612; G01N 1/02; G01N 2001/028; G01N 2001/2833; G01N 2021/4707; G01N 2021/8864; G01N 2021/8887; G01N 21/4738; G01N 21/8901; G01N 21/909; G01N 21/956; G01N 33/36; G01N 33/362; G01N 15/08; G01N 2015/0846; G01N 2015/144; G01N 2015/145; G01N 2015/1452; G01N 2021/8681; G01N 2021/8848; G01N 2021/891; G01N 2021/8917; G01N 21/21; G01N 21/255; G01N 21/276; G01N 21/278; G01N 21/3563; G01N 21/359; G01N 21/474; G01N 21/55; G01N 21/59; G01N 21/64; G01N 21/84; G01N 21/8851; G01N 21/8914; G01N 21/892; G01N 21/8921; G01N 21/8922; G01N 21/894; G01N 21/896; G01N 2201/0612; G01N 2201/062; G01N 2201/08; G01N 2201/10; G01N 2201/1293; G01N 2203/0023; G01N 2203/028; G01N 2203/0282; G01N 22/04; G01N 27/228; G01N 27/24; G01N 27/44791; G01N 3/08; G01N 3/20; G01N 2021/1748; G01N 2021/6419; G01N 2021/6421; G01N 2021/6439; G01N 2021/6463; G01N 21/0303; G01N 21/05; G01N 21/251; G01N 21/33; G01N 21/534; G01N 21/6408; G01N 21/6428; G01N 21/6454; G01N 21/648; G01N 21/78; G01N 2201/0696; G01N 2201/12; G01N 33/32; G01B 11/02; G01B 11/024; G01B 11/08; G01B 11/14; G01B 11/26; G01B 15/025; G01B 11/0616; G01B 7/085; G01J 3/50; G01J 3/501; G01J 3/51; G01J 3/513; G01J 3/524; G02B 6/04; G02B 6/3574; G02B 6/3598; G02B 6/3616; G02B 6/4206; G02B 6/443; G02B 19/0009; G02B 19/0014; G02B 19/0052; G02B 19/0057; G02B 1/10; G02B 26/103; G02B 27/0955; G02B 27/0096; G02B 27/123; G02B 27/30; G02B 6/02004; G02B 6/02033; G02B 6/03633; G02B 6/12; G02B 6/1221; G02B 6/132; G02B 6/28; G02B 6/30; G02B 6/32; G02B 6/3846; G02B 6/421; G02B 6/4214; G02B 6/4246; G02B 6/425; G02B 6/4427; G02B 6/4492

See application file for complete search history.

(56) References Cited

U.S. PATENT DOCUMENTS

| | | | |
|---|---|---|---|
| 2003/0107729 A1* | 6/2003 | Furter | ................ G01N 21/8915 356/238.1 |
| 2005/0213113 A1 | 9/2005 | Sikora et al. | |
| 2006/0098201 A1* | 5/2006 | Birlem | ................ G01N 21/8915 356/429 |
| 2009/0103111 A1 | 4/2009 | Spalding | |
| 2011/0299095 A1 | 12/2011 | Morgan et al. | |

FOREIGN PATENT DOCUMENTS

| | | |
|---|---|---|
| DE | 100 03 717 A1 | 7/2001 |
| DE | 102 19 848 A1 | 10/2003 |
| DE | 10 2006 010 992 A1 | 9/2007 |
| EP | 0 692 697 A2 | 1/1996 |
| GB | 2 160 654 A | 12/1985 |
| JP | 2000-0161985 A | 6/2000 |
| WO | 2009/150620 A1 | 12/2009 |

OTHER PUBLICATIONS

International Search Corresponding to PCT/IB2017/000372 dated Jun. 26, 2017.
Written Opinion Corresponding to PCT/IB2017/000355 dated Jun. 26, 2017.
Written Opinion orresponding to PCT/IB2017/000372 dated Jun. 26, 2017.

* cited by examiner

COMBINATION SENSOR

This application is a National Stage completion of PCT/IB2017/000355 filed Mar. 31, 2017, which claims priority from European patent application serial no. 16163595.8 filed Apr. 1, 2016.

FIELD OF THE INVENTION

The invention relates to an arrangement for automatically detecting elongate objects such as cables, wires or profiles using at least two optical measuring systems based on different measurement methods and an installation using such an arrangement.

BACKGROUND OF THE INVENTION

In processing machines for cable, wires or similar elongate objects, it must be ensured by reliable identification of the objects that the type of processing, the settings of the machine and their parameters are tuned to the respective object and the requirements defined by the user. To this end measuring systems are preferably arranged in front of or at the input of the processing machine, which should enable a reliable identification of the elongate object. These comprise a plurality of sensor arrangements since the reliability of the identification increases with the number of different measurement principles (because, for example, cable having the same outside diameter and the same colour can have different internal conducting configurations or cable having a different structure—fine braid, braid, wire—with a different copper cross-section can have the same electromagnetic characteristics).

DE10219848A1 discloses a contactless centricity and diameter measuring system comprising an optical measuring device for determining the outside diameter and the position of an elongate object in an optical measurement plane arranged perpendicular and transversely to the central axis of a measuring device. The object comprises a conductor and a sheath which insulates this, wherein the position of the conductor in an inductive measurement plane is determined by means of an inductive measuring coil device, whose measurement plane is also arranged perpendicular and transverse to the central axis of the measuring device. The position of the object determined by the optical measuring device is related to the position of the conductor determined by the inductive measuring coil device and from this the centricity of the conductor in the sheath is calculated. In this case the measuring coils of the measuring coil device are arranged in pairs or equally in relation to the optical measurement plane but are not traversed by the elongate object. The measurement object itself always remains outside the measuring coils. The pairwise arrangement of coils is used for differential measurement of the field strength, starting from the alternating current flowing in the conductor, which must be induced by means of an additional inductor of the measuring system in the conductor. Thus, the different of the voltages induced in the coils is a measure of the eccentricity of the conductor in relation to the coil mirror axis. The coils are therefore not part of a resonant circuit which is damped by the copper. Furthermore, no further optical measuring system is provided.

WO2009150620A1 in turn describes an arrangement of sensors, which as a result of measurements of the outside diameter of a cable, the diameter of the metallic conductor lying inside the insulating sheath and optionally other externally detectable features allows an automatic or semi-automatic identification of the respective cable provided for processsing or at least the cable type. The various said sensors are functionally independent of one another, have no synergistic effects, have no jointly used element or areas and therefore do not form a combination of measuring systems.

SUMMARY OF THE INVENTION

It is the object of the present invention to provide an improved sensor arrangement which uses synergies of various measuring systems so that a compact, functionally robust design of a combination sensor is obtained which enables the determination of several characteristics of the object in order to enable a reliable identification of the object to be made from this.

In order to solve this object, the initially described arrangement is characterized in that at least a first optical measuring system for determining the outside diameter of the object and at least a second optical measuring system for determining the colour of the object form a combination with a common measurement volume. In a preferred embodiment this measurement volume is disk-shaped. The first measuring system for determining the outside diameter comprises at least a first illumination arrangement and a first sensor array positioned on the opposite side of the measurement volume, wherein a lens is arranged between the first illumination arrangement and the measurement volume, which lens is designed and positioned as a collimating lens for the light of the first illumination arrangement and wherein the second measuring system comprises at least one second illumination arrangement, a second sensor array, and a long-pass filter, wherein this is arranged between the first illumination arrangement and the lens), is reflecting for the wavelength spectra of the second measuring system and transmitting for the light of the first measuring system and together with the lens is designed and positioned so that this is passed twice by the reflected light of the object and projects an image of the object onto the second sensor array. The combination of several measuring systems increases the identification quality for the type or the nature of the elongate object, for example the type of a cable to be processed in a cable processing installation. It is thereby ensured that the parameters of the cable processing correspond to the type or only suitable cable is processed on the respective machine. The arrangement also allows a very precise determination of the diameter of the elongate object with a relatively simple constructive design with conventional and proven components. The light source can illuminate the object advantageously through the cap of the guide device, whose shadow is also incident through this gap on the first sensor array and can be defected there. Since cable types are frequently, for example characterized by the colours of their sheathing, such a sensor arrangement using different wavelength spectra and the reflected intensities thereof allows a rapid and very secure identification of the cable type.

Preferably the disk-shaped measurement volume is arranged between the both-side ends of the guide device, preferably in the longitudinal direction centrally and preferably coaxially to the guide device. This guide device can, for example be a cable jack through which a cable is guided as elongate object to be identified. Thus, various measured values and characteristics of the object can be detected by a relatively compact arrangement in order to allow its rapid identification with high reliability.

Preferably the principal plane of the optical measuring systems is arranged with the principal optical axis perpendicular to the longitudinal axis of the guide device for the elongate object.

Advantageously the first illumination arrangement comprises a light source and at least one screen.

Preferably the second illumination arrangement comprises a plurality of, preferably three and also preferably placed close to one another, light sources having different wavelength spectra and the second sensor array for the light reflected from the object lies in relation to the x-z plane on the same side of the disk-shaped measurement volume as the second illumination arrangement. The light sources of this illumination arrangement are preferably placed such and their light cones are formed with a screen such that their light is not incident on the sensor housing but only on the object to be measured.

Preferably a sequence is implemented in the second measuring system to drive the light sources of the second illumination arrangement in such a manner to sequentially illuminate the object and thus sequentially project an image in the wavelength spectra of the light sources onto the second sensor array. This second sensor array is for its part connected to an evaluation unit for the intensities measured during the illumination with the light sources of different wave length spectra and for the ensuring determination of the colour of the object.

An advantageous embodiment of this arrangement is characterised according to the invention in that the long-pass filter is arranged on the principal optical axis and preferably is aligned in such a manner in order to deflect the light reflected by the object onto the second sensor array positioned outside the principal optical axis and aligned onto the long-pass filter for detection of the colour.

Preferably according to the present invention, the optical measuring system for determining the diameter and the optical measuring system for determining the colour are combined to form a third virtual measuring system for determining the position of the object inside the disk-shaped measurement volume. The individual optical measurements and the inductive measurement can thus be corrected by incorporating the position information for the object in order to obtain more accurate measurement results.

A further embodiment of the invention provided that the third measuring system comprises a third illumination arrangement with preferably two light sources, the first sensor array and optionally the first illumination arrangement for triangulatory determination of the position of the object inside the measurement volume.

An alternative embodiment for the light sources for the colour determination comprises that in which the luminaires of the third illumination arrangement comprises a plurality of light sources each having different wavelength spectra and designed to illuminate the object sequentially and thus sequentially project an image in the wavelength spectra of the light sources onto the second sensor array.

Common to all the arrangements is the advantageous feature of the invention that the measurement plane of the first sensor array runs perpendicular to the x-y plane but can intersects this at a small angle to the x axis to avoid reflection. This is particularly important if the two locations of the light sources for determining position are also used as locations for light sources for determining colour.

An alternative embodiment can be characterised in that the second sensor array for determining colour is a multichromatic sensor and the light sources of the second illumination arrangement are operated simultaneously or are replaced by a wide-band or multiband light source.

Alternatively or additionally it can also be provided for this purpose that the second sensor array is a multichromatic sensor and at least one of the light sources of the second illumination arrangement is replaced by a wide-band or multiband light source.

Advantageously the arrangement can also be provided with a temperature sensor for correction of the temperature-induced measurement errors.

In order to solve the initially formulated object, an installation for processing elongate objects such as cables, wires or profiles is also described with an arrangement for automatic detection of objects positioned on one side as in the preceding paragraphs.

Further advantages, features and details of the invention are obtained from the following description in which exemplary embodiments of the invention are described with reference to the drawings. In this context, the features mentioned in the claims and in the description are each essential to the invention individually for themselves or in any combination.

The technical content of the patent claims and figures is part of the disclosure. The figures are described in a cohesive and overlapping manner. The same reference numbers mean the same components, reference numbers with different indices specify functionally the same or similar components.

DETAILED DESCRIPTION OF THE PREFERRED EMBODIMENTS

Figure 1:
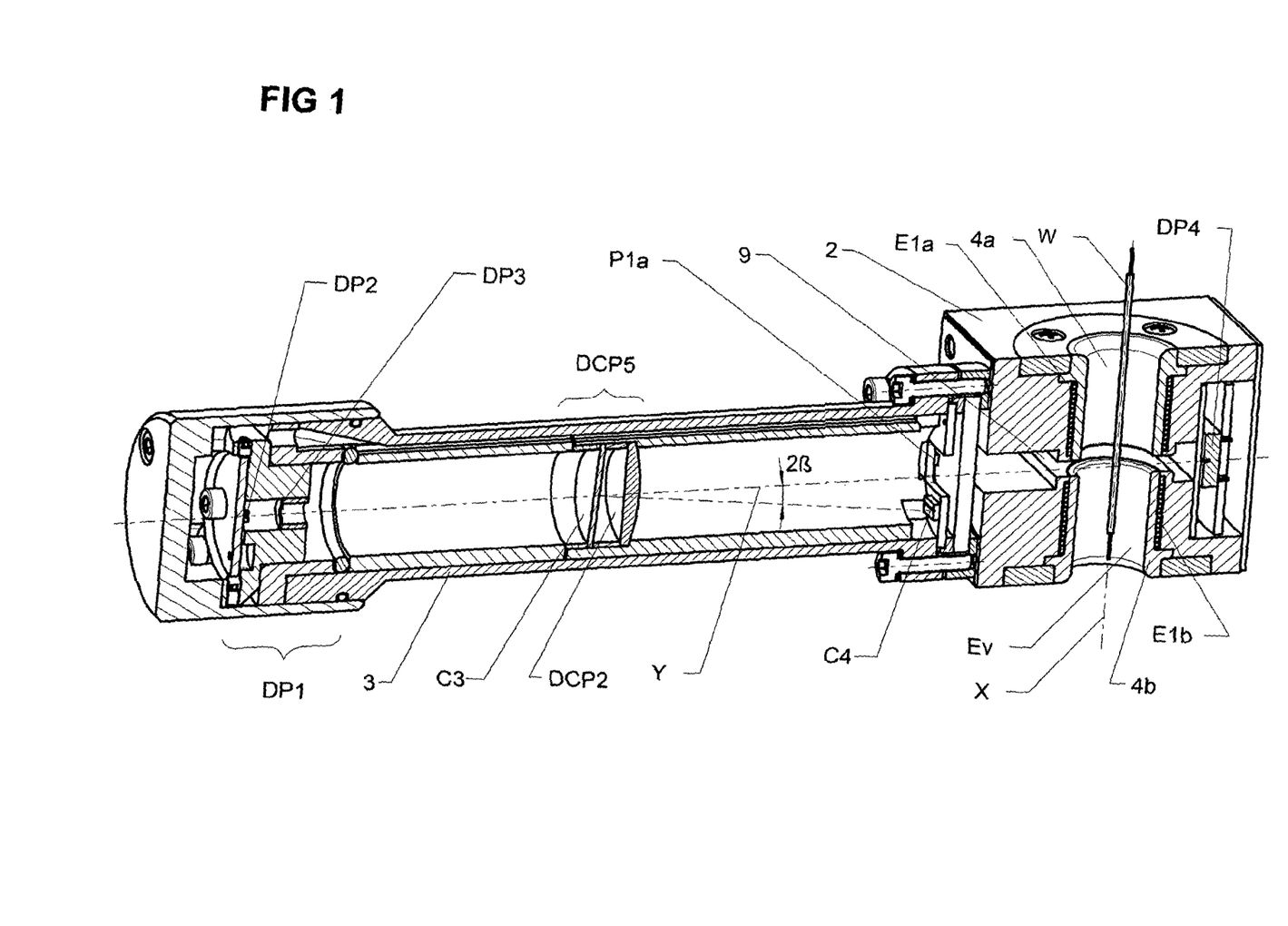
FIG. 1 shows a longitudinal section in the x-y plane through an exemplary sensor arrangement according to the invention for a cable processing machine.

FIG. 1 shows an exemplary embodiment of a sensor arrangement such as is preferably positioned in front of or at the input of a processing machine for elongate objects, in particular for processing machines for cable or the like in order to enable a reliable identification of the cable to be processed as measurement object W. On the input side a housing 2 as well as a tube 3 with a part of the optical system of the sensor arrangement are fastened on the processing machine. The elongate object W is guided in the axial direction and before the beginning of the actual processing through the cable jacks 4a, 4b as a guide device in the housing 2.

During the through-movement of the object W or also during a standstill time, the outside diameter and the colour of the object W are determined. In addition, the position of the object inside the cable jacks 4a, 4b can be determined. The sensors for determining these measured quantities and therefore the measuring systems for the outside diameter or colour of the object W are based according to the invention on different measurement principles but at least partially use joint areas or elements of the sensor arrangement.

FIG. 1 shows a section through the sensor arrangement in the plane which is defined by the optic axis y and the axis x of the cable jacks 4a and 4b. Positioned at the outermost end of the tube 3 is a first illumination arrangement DP1 of the first optical measuring system D for determining the diameter with a light source DP2 and the screen DP3. The first optical measuring system D can also be part of another optical measuring system P for determining the position of the object W. An imaging optical system DCP5 is installed between the object W and this first illumination arrangement DP1, of which the long-pass filter C3, which acts as a mirror for visible light, reflects the light reflected by the object W and directs it onto a second sensor array C4, preferably the linear sensor array C4, of the measuring system C for detecting the colour of the object W. The housing 2 also accommodates another first sensor array as defector for the optical measuring system D for determining the diameter, preferably a linear sensor array DP4. The measuring systems C, D described above can in any case be linked to form a third virtual measuring system P, as will be explained further below.

The essential elements of the measuring systems D, C, P are again shown schematically in FIGS. 2 and 3 and in their advantageous mutual arrangement and will be explained in detail hereinafter. In any case, a combination of the optical measuring arrangement shown here with further measuring arrangement on a completely different basis is expedient, for example with an eddy current sensor comprising a coil E1, which consists of the two half-coils E1a and E1b and the capacitor E2, which together form a resonant circuit E6 of an inductive measuring system. This measuring system which also includes the exciter circuit E3, the resistor E4 and a signal converter E5, allows the measurement of an electromagnetic characteristic of the elongate object, from which preferably the cross-section of the conducting component of the object W, in particular the cross-section of the conductor or conductors of the cable can be determined.

The two cable jacks 4a, 4b are slightly spaced apart from one another in the axial direction, with the result that a gap 9 is obtained between these two components, which is continued in the housing 2 and enables access to the object W inside the cable jacks 4a, 4b for the optical measuring systems D, C, P. The joint partial volume which is obtained through gap 9 and the cable guide opening, forms a disk-shaped optical measurement volume DCPv.

Figure 2:
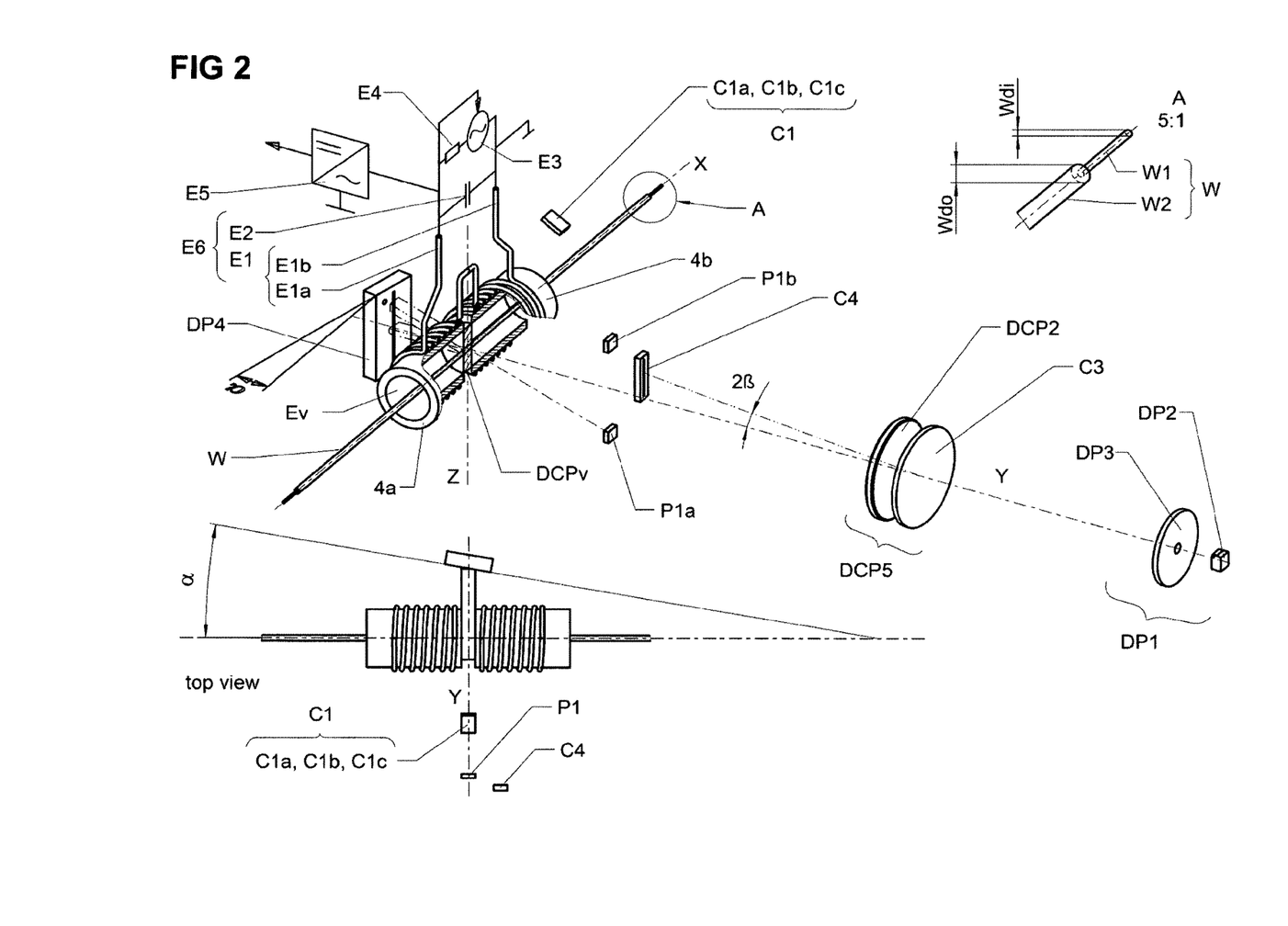
FIG. 2 shows a diagram of the measuring systems of the arrangement from FIG. 1.

It is furthermore also deduced from FIG. 2 that preferably the principal plane y-z of the optical measuring systems D, C, P in which the principal optic axis y also lies is oriented perpendicular to the longitudinal axis x of the cable jacks 4a, 4b.

For optical measurement of the outside diameter of the object W this is illuminated inside the cable jack 4a, 4b in the area of the optical measurement volume DCPv through the gap 9. As is shown clearly in FIG. 5, the light of the first illumination arrangement DP1 is collimated by the optical system DCP5 of the measuring system D, impinges upon the object W and causes a shadowing symbolized by S1. As is depicted schematically in FIG. 1, this shadowing S1 causes different voltage levels for each pixel on the first linear sensor array DP4, from the distribution of which the cable diameter can be concluded. Advantageously the measurement plane of the linear sensor array DP4 runs perpendicular to the x-y plane but can intersect this at a small angle $\alpha$ to the x-axis (see FIG. 2).

The parallelism of the light and the pixel width of the sensor DP4 are crucial for the accuracy of the measurement. The light of the first illumination device DP1 with light source DP2, preferably designed as infrared LED, passes through the long-pass filter C3 uninfluenced and is collimated by the lens DCP2. For other wavelengths, in particular in the wavelength range of the visible light, however the long-pass filter C3 behaves as a mirror.

The disk-shaped optical measurement volume DCPv is used for determining the diameter and for detecting the colour of the object W, which results in a substantial saving of installation size. The second measuring system C provided for this purpose comprises, as can be deduced from FIGS. 2 and 3, a second illumination arrangement C1 having a plurality of light sources C1a, C1b, C1c placed close to one another having different wavelength spectra. Preferably three light sources are provided. The light-sources are, for example designed as coloured LEDs (e.g. PGB-LEDs).

In this case, a sequence is implemented in the measuring system C, for example as an executable program in a control and evaluation unit of this measurement system, by means of which the light, sources C1a, C1b, C1c of the second illumination arrangement C1 are driven in such a manner in order to sequentially illuminate the object W and therefore sequentially project an image in the wavelength spectra of the light sources onto a second sensor array C4 of this measurement system C. In the evaluation unit of the optical measurement system C the intensities measured during illumination of the object W using the light sources having different wavelength spectra are used for determining the colour of the object W. The second sensor array C4 is located—see on this matter FIG. 1 and FIG. 2—in relation to the x-z plane on the same side of the disk-shaped measurement volume DCPv as the light sources C1a, D1b, C1c of the second illumination arrangement C1. Alternatively to the second sensor array C4, which is sensitive for the wavelengths of all three light sources, a multichromatic sensor consisting of three sensors sensitive for respectively different wavelengths could be provided.

The long-pass filter C3 positioned on the principal axis y of the optical measurement system D, C, P is reflecting for the wavelengths of the light sources C1a, C1b and C1c of the second illumination arrangement C1 and thereby reflects the light reflected from the object W onto the second sensor, array C4 positioned outside the principal optical axis y. The long-pass filter C3 is therefore penetrated by the light of the first illumination arrangement DP1 which then passes through the lens DCP2 and is thereby collimated. Light of the first illumination arrangement C1 then passes twice through the lens DCP2 as imaging lens—after reflection by the object W and also after reflection at the long-pass filter C3—so that its refractive power is used twice and the imaging focal width is almost halved. The image is therefore formed somewhat laterally of the optic axis y if perpendicular the long-pass filter C3 reflecting in the measurement system C is arranged in the x-y plane at a small angle β to the principal optical axis y.

Figure 6:
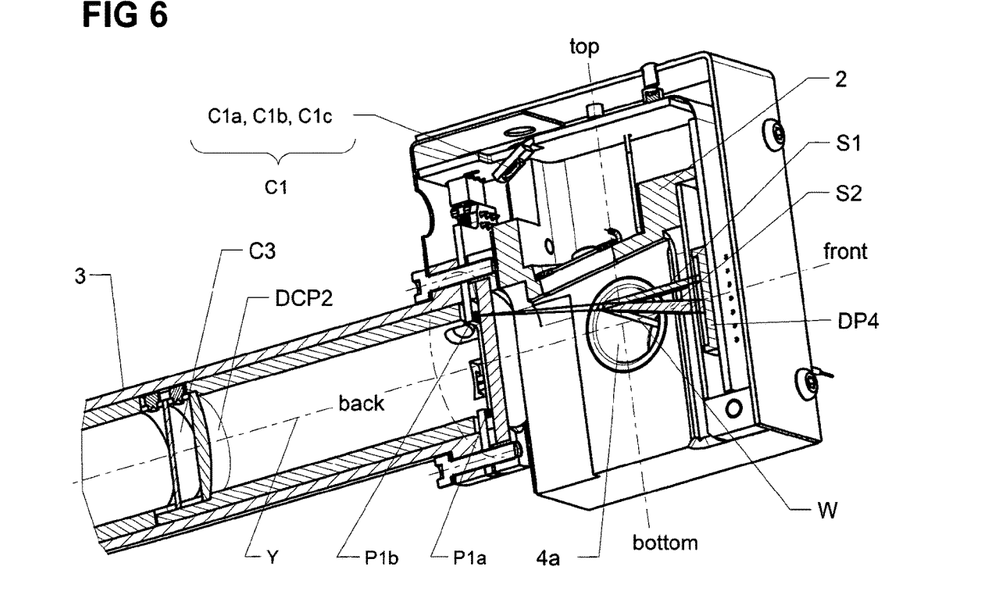
FIG. 6 shows another longitudinal section in the y-z plane through the sensor arrangement.

In order to determine the cable colour, preferably three images are made sequentially by means of the second sensor array by means of respectively different illumination, for example under red, green and blue light. The colour of the object W can then be calculated in the evaluation unit through the project colour intensities. It should be noted here that the colour intensity measured by the second sensor array C4 decreases quadratically with respect to the distance between the light sources and the object W and quadratically with respect to the distance between object W and lens DCP2. This cable location dependence can for example be corrected with adapted exposure time. Where the cable is located inside the optical measurement volume DCPv can be calculated by means of a simple triangulation with two shadow edges as shown in FIG. 6. With the aid of the cable position, a correction of the output signals of the second sensor array C4 can be made for the respective wavelength by interpolation between intensity correction values determined empirically in the measurement volume DCPv.

For the location-dependent compensation of the measured values, preferably the first optical measurement system D for the diameter measurement is combined with two further light sources P1a and P1b to form a third, virtual optical measurement system P for determining the position of the object W within the disk-shaped measurement volume DCPv. This additional optical measurement system P uses at least two of the light sources P1a, P1b, DP2 of the optical measurement systems explained above and the first linear sensor array DP4.

Alternatively, one of the light sources, in particular the light source of the illumination arrangement DP1 can be combined with an additional light source when the diameter measurement is provided alone. Only a spacing of the light sources used in the circumferential direction of the cable jacks 4a, 4b or the disk-shaped optical measurement volume DCPv is important here. These two light sources yield different-angle shadowings S1, S2 whose spacing is determined with the aid of the first sensor array DP4 and on the basis of the known geometrical relationships can be converted into location information for the object W inside the cable jacks 4a, 4b or the inductive measurement volume Ev and also the optical measurement volume DCPv.

A specific design example of the geometrical optics of one embodiment of the sensor arrangement according to the invention for detecting cable colour is presented hereinafter.

Figure 7:
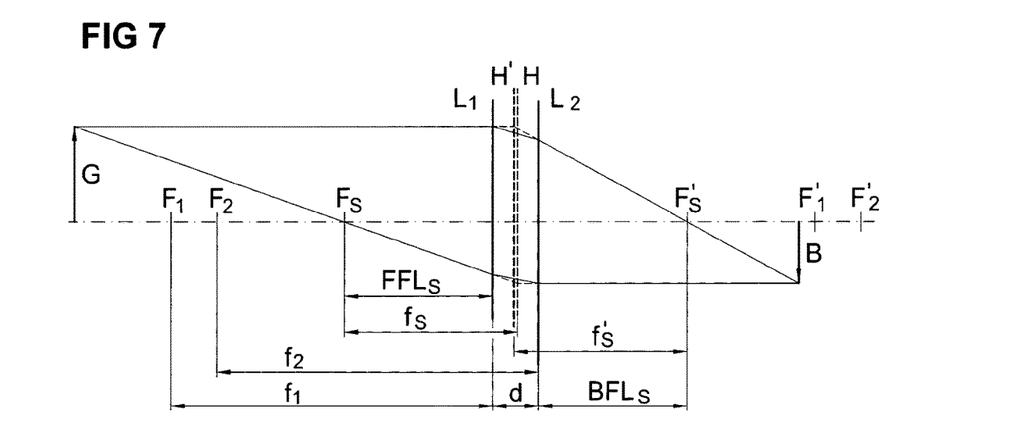
FIG. 7 shows the optical relationships of a sensor arrangement with a double lone system.

FIG. 7 shows a double lens system with two identical lenses $L_1$ and $L_2$, their appurtenant focal points $F_1$ and $F_2$, their respective focal widths $f_1$ and $f_2$, the object to be imaged G and the image B. The lenses $L_1$ and $L_2$ are located at a distance d from one another. In order to simplify the beam path and optical calculations, the double lens system can be replaced by a single lens with its principal planes H and H' and its appurtenant system focal points $F_s$ and $F_3'$. The distance from $F_3$ to $L_1$ is also called $FFL_s$ (front focal length) and the distance from $F_s'$ to $L_2$ $BFL_s$ (back focal length).

Here it holds that:

$$\frac{1}{FFL_s} = \frac{1}{f_1} + \frac{1}{f_2 - d} \quad 1)$$

$$FFL_s = \frac{f_1(f_2 - d)}{(f_1 + f_2) - d} \quad 2)$$

$$\frac{1}{BFL_s} = \frac{1}{f_2} + \frac{1}{f_1 - d} \quad 3)$$

$$BFL_s = \frac{f_2(f_1 - d)}{(f_1 + f_2) - d} \quad 4)$$

$$\frac{1}{f_s} = \frac{1}{f_1} + \frac{1}{f_2} - \frac{d}{f_1 f_2} \quad 5)$$

$$f_s = \frac{1}{\frac{1}{f_1} + \frac{1}{f_2} - \frac{d}{f_1 f_2}} = \frac{f_1 f_2}{f_1 + f_2 - d} \quad 6)$$

Figure 8:
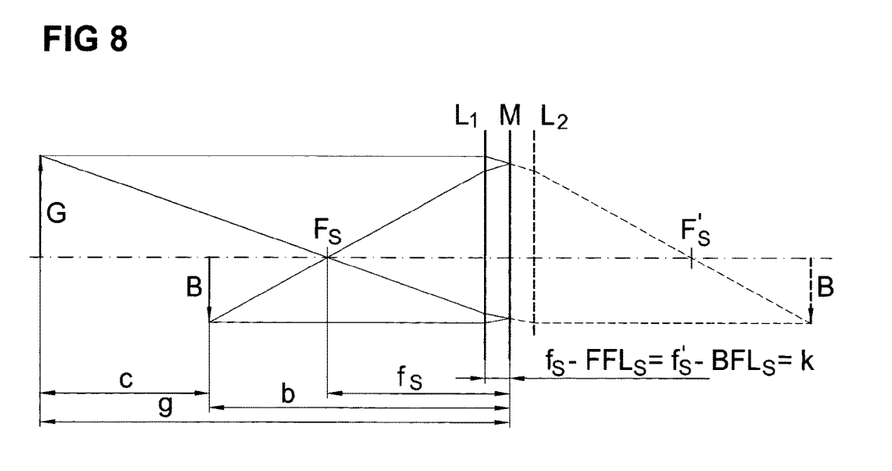
FIG. 8 shows the optical relationships of a sensor arrangement with a double lens system with mirrors.

FIG. 8 shows the double lens system when a mirror M is placed in the principal plane H. This has the effect that image B can be projected on the object side and $L_2$ omitted since $L_1$ additionally also takes on the function of $L_2$. FIG. 8 therefore schematically shows the optical situation in the optical measurement system C explained above for the cable colour, as is shown most clearly in FIGS. 2 and 3. The reflecting long-pass filter C3 corresponds to the mirror M and the lenses $L_1$ or $L_2$ correspond to the collimating lens DCP2.

With the wedge-shaped pipe piece of the optical system DCP5 in FIG. 1 between mirror M and lens $L_1$, the distance k=6.575 mm between M and $L_1$ is given. With reference to FIG. 7 and FIG. 8, the distance d between the lenses $L_1$ and $L_2$ can be calculated as follows:

$$k = f_s(d) - FFL_s(d) \quad 7)$$

$$k = \frac{f_1 f_2}{f_1 + f_2 - d} - \frac{f_1(f_2 - d)}{(f_1 + f_2) - d} \quad 8)$$

$$k = \frac{f^2}{2f - d} - \frac{f^2 - fd}{2f - d} \quad 9)$$

$$(2f - d)k = fd \quad 10)$$

$$fd + kd = 2fk \quad 11)$$

$$d = \frac{2fk}{f + k} \quad 12)$$

$$d = \frac{2 \cdot 71 \cdot 6.575}{71 + 6.575} = 12.035 \quad 13)$$

Using formula 6 and for f=71 mm, the system focal width $f_s$ should now be calculated:

$$f_s = \frac{71 \cdot 71}{71 + 71 - 12.035} = 38.787 \quad 14)$$

Figure 3:
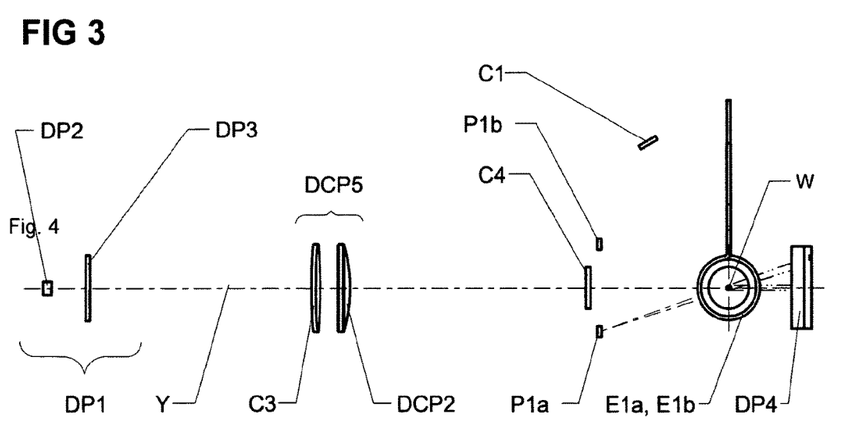
FIG. 3 shows a schematic view of the measuring systems according to FIG. 1 in the axial direction of the elongate object.
Figure 4:
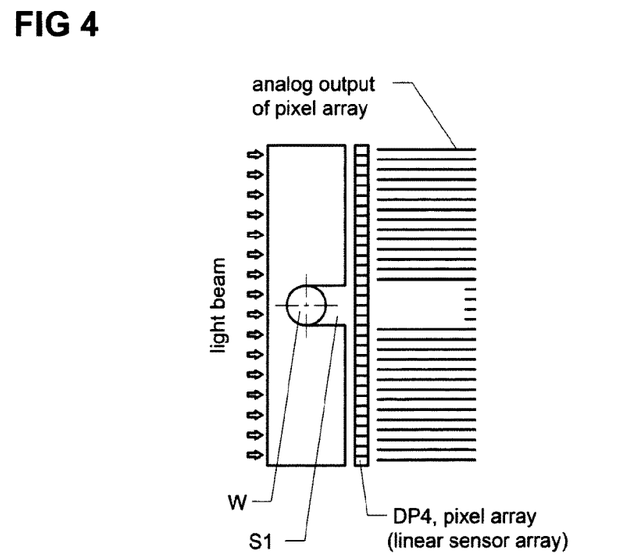
FIG. 4 shows schematically the functional diagram of a sensor arrangement according to the invention for measuring the diameter of a cable.
Figure 5:
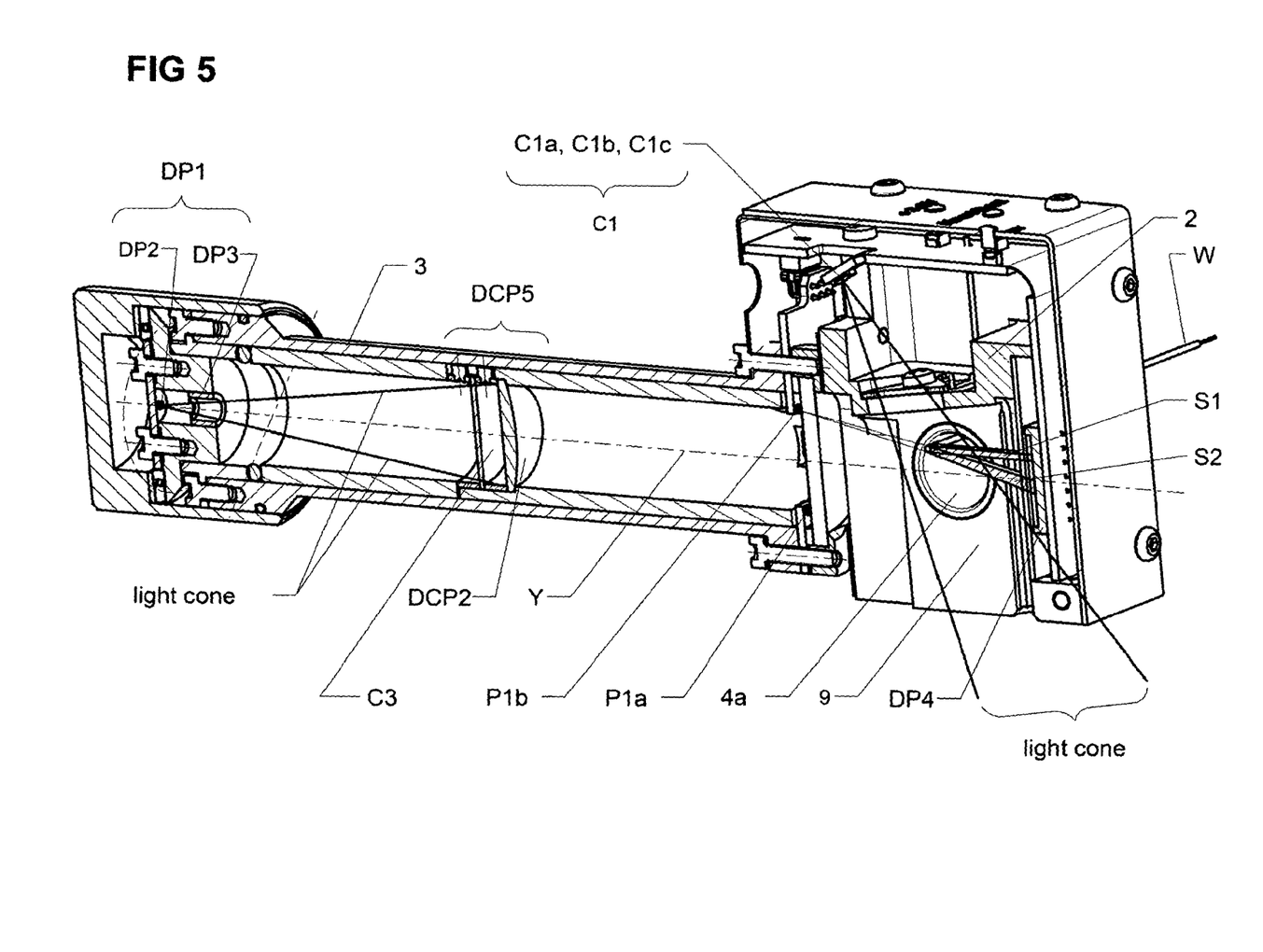
FIG. 5 shows a longitudinal section in the z-y plane through a sensor arrangement according to the invention along the optic axis.

In the design from FIG. 2, FIG. 3 and FIG. 5, a c value (distance from the object G to the image B, i.e. from the longitudinal axis x to the second sensory array C4) of 33.5 mm was obtained. The question now arises as to how large the distances b (sensor–mirror) and g (longitudinal axis x–mirror C3) must be so that a sharp image is obtained at the second sensor array C4.

This is obtained as follows (where c=33.5 mm):

$$\frac{1}{f_s} = \frac{1}{g} + \frac{1}{b} \quad \text{15)}$$

$$g = c + b \quad \text{16)}$$

$$\frac{1}{f_s} = \frac{1}{c+b} + \frac{1}{b} \quad \text{17)}$$

$$\frac{1}{f_s} - \frac{1}{b} = \frac{1}{c+b}$$

$$\frac{b - f_s}{f_s b} = \frac{1}{c+b}$$

$$(b - f_s)(c + b) = f_s b$$

$$bc + b^2 - f_s c - f_s b = f_s b$$

$$b^2 + bc - 2f_s b - f_s c = 0$$

$$b^2 + b(c - 2f_s) - f_s c = 0$$

$$b = \frac{(2f_s - c)}{2} \pm \sqrt{\frac{(c - 2f_s)^2}{4} + f_s c} \quad \text{18)}$$

$$b = \frac{(2 \cdot 38.787 - 33.5)}{2} \pm \sqrt{\frac{(33.5 - 2 \cdot 38.787)^2}{4} + 38.787 \cdot 33.5} \quad \text{19)}$$

$$b = 22.037 \pm 42.249 = 64.286$$

$$g = 33.5 + 64.286 = 97.786 \quad \text{20)}$$

Since all the dimensions are now given, the imaging scale M can be calculated.

$$M = \frac{b}{g} = \frac{B}{G} \quad \text{21)}$$

$$M = \frac{64.286}{97.786} = 0.657 \quad \text{22)}$$

For a second sensor array C4 having a resolution of 400 dpi and 128 pixels this gives an active sensor array length ISA:

$$I_{SA} = \frac{25.4 \cdot 128}{400} = 8.13 \text{ mm} \quad \text{23)}$$

A maximum object size to be imaged is thus obtained as $$G = \frac{B}{M} = \frac{I_{SA}}{M} = \frac{8.128}{0.657} = 12.37 \text{ mm} \quad \text{24)}$$

Figure 9:
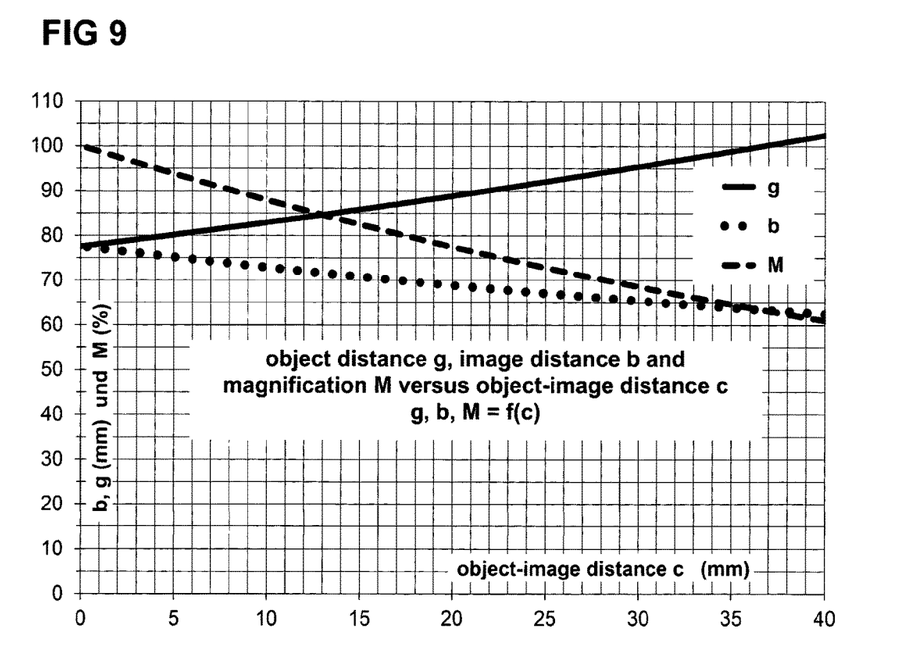
FIG. 9 shows a diagram with image width, object width and image scale as a function of the object-image distance

Using the system focal width $f_s$ of the lens from formula 14, as shown in FIG. 9, the image width b and the object width g can be plotted graphically as a function of the object-image distance c, i.e. the longitudinal axis x—second sensor array C4—distance for the specific exemplary embodiment using Equation 18.

Figure 10:
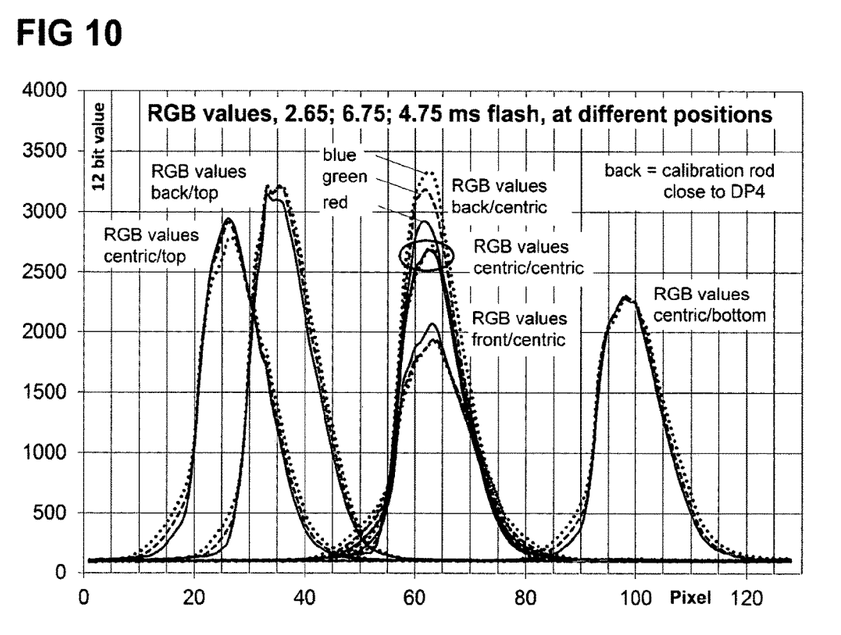
FIG. 10 shows a diagram for the white balance of a sensor arrangement and FIG. 11 shows a diagram with the measured values of an orange-coloured cable.

When the object-sensor distance c tends to 0, the imaging scale, as can be identified in FIG. 10, tends to 100%. This is the known 1/1 imaging with $g=b=2*f_s$.

Before the cable colour can be measured with the second sensor array C4, a white balance must be performed. To this end a white calibration rod is placed in the cable jacks 4a, 4b in such a manner that it lies as close as possible to the second illumination arrangement C1, so that the sensor array C4 measures the greatest brightness. The maximum allowed illumination times during illumination at the different wavelengths (red, green, blue) are adjusted so that the measured amplitudes account for about 90% of the measurement range. The calibration rod is then placed in the longitudinal axis x and the exposure times are adjusted to that the RGB integral values measured by the second sensor array C4 are all the same. In so doing, the two higher integral values are adapted to the lowest so that the previously determined maximum exposure times are not exceed by any colour (see FIG. 10). Since the brightness of the image decreases with increasing distance between light source and object W and between object W and lens DCP2, the brightness values for the different wavelengths must be weighted according to cable position. In FIG. 10 for example, RGB measured values are plotted for six calibration rod positions inside the cable jacks 4a, 4b: the curves designated by "centric/centric" are valid for the white calibration rod at the centre of the cable jacks 4a, 4b. If the calibration rod is located in the cable jacks 4a, 4b close to the second sensor array C4, the lines designated by "back/centric" apply. In FIG. 6 the location information back, front, bottom, top is characterized so that the measured values plotted in FIG. 10 can be correctly interpreted.

The ratio of the RGB integral values of a specific location measured with a calibration rod to the RGB integral values of the centre are colour correction values. They are dependent on location.

Figure 11:
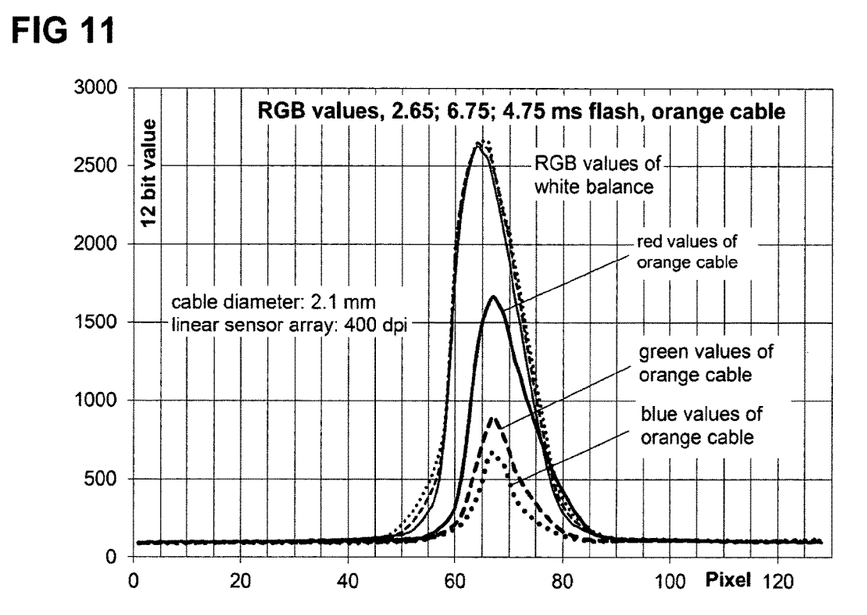

FIG. 11 finally shows RGB measured values of an orange cable as object W at the centre of the cable jacks.

In addition to the already-mentioned advantages of the quasi-coaxial arrangement of the measurement systems D, C and P such as compact, robust, mechanical and functional synergy-using design, another advantage is that many circuit pares of the electronics such as communication interface, microcontroller, supply, LED displays and suppressor circuits can be used for all three sensors or systems D, C and P.

The greater is the focal width of the lens DCP2 for the collimation, the better is the collimation, i.e. the parallelism of the light and the more sharp-edged is the shadowing for the diameter measured. A large focal width of the lens DCP2 is also advantageous for the colour determination since then the cable-lens distance g is greater and therefore the image sharpness for the colour detection is maintained even if the object W should not run centrally through the cable jacks 4a, 4b. With increasing focal width however for the diameter measurements and also for the colour determination, the light intensity decreases which must be compensated by a longer exposure time so that for both functionalities a compromise between light intensify and image sharpness must be found.

The above-explained arrangement for the automatic defection of elongate objects using purely optical measurement systems D, C, P can, if required be linked not only to an inductive measurement system E but also to other measurement systems. In cable processing installations devices for cutting to length or insulating the cable are frequently provided which comprise clamping jaws and blades which can be moved with respect to one another. For such installations the measurement systems D, C, P, E can be combined with at least one further measurement system which is provided for determining the outside diameter of the object by means of a measurement of the clamping jaw spacing or for determining the diameter of an electrical conductor within the object based on a measurement of a blade spacing at the time of a blade-conductor contact. Measurement arrangements on an electrical basis, in particular by monitoring capacitive and/or inductive characteristics are sufficiently known.

The use of a temperature sensor combined with the measurement systems D, C, P, E is advantageous to compensate for temperature-induced measurement errors. In this case, preferably a correction sequence in the respective measurement system is implemented for an automated compensation in order to provide its measured value with a correction factor as a function of the temperature and with a correction factor as a function of the cable location.

The invention claimed is:

1. An arrangement for automatic contactless detection of elongate objects (W), comprising at least two optical measuring systems (D, C) based on different measurement methods,
   wherein at least a first optical measuring system (D) for determining an outside diameter (Wdo) of the object (W) and at least one second optical measuring system (C) for determining a color of the object (W) from a combination with a common disk-shaped measurement volume (DCPv),
   the first measuring system (D) comprises at least a first illumination arrangement (DP1) and a first sensor array (DP4) positioned on the opposite side of the measurement volume (DCPv),
   a lens (DCP2) is arranged between the first illumination arrangement (DP1) and the measurement volume (DCPv), which lens is designed and positioned as a collimating lens for light of the first illumination arrangement (DP1), and
   the second measuring system (C) comprises at least one second illumination arrangement (C1), a second sensor array (C4), and a long-pass filter (C3), this is arranged between the first illumination arrangement (DP1) and the lens (DCP2), is reflecting for the wavelength spectra of the second measuring system (C) and transmitting for the light of the first measuring system (D) and together with the lens (DCP2) is designed and positioned so that this is passed twice by the reflected light of the object (W) and projects an image of the object (W) onto the second sensor array (C4).

2. The arrangement according to claim 1, wherein the disk-shaped measurement volume (DCPv) is arranged between both-side ends of the guide device (4a, 4b).

3. The arrangement according to claim 1, wherein a principal plane (y-z) of the first and second optical measuring system (D, C) is arranged with the principal optical axis (y) perpendicular to the longitudinal axis (x) of the guide device (4a, 4b) for the elongate object (W).

4. The arrangement according to claim 1, wherein the first illumination arrangement (DP1) comprises a light source (DP2) and at least one screen (DP3).

5. The arrangement according to claim 1, wherein the second illumination arrangement (C1) comprises a plurality of light sources (C1a, C1b, C1c) having different wavelength spectra and that the second sensor array (C4) for the light reflected from the object (W) lies in relation to an x-z plane on a same side of the disk-shaped measurement volume (DCPv) as the second illumination arrangement (C1).

6. The arrangement according to claim 5, wherein a sequence is implemented in the second measuring system (C) to drive the light sources (C1a, C1b, C1c) of the second illumination arrangement (C1) in such a manner to sequentially illuminate the object (W) and thus sequentially project images in the wavelength spectra of the light sources of the second illumination arrangement (C1) onto the second sensor array (C4), this is connected to an evaluation unit for intensities measured during the illumination with the light sources of different wavelength spectra and for ensuing determination of the color of the object (W).

7. The arrangement according to claim 1, wherein the long-pass filter (C3) is arranged on a principal axis (y) and is aligned in such a manner in order to deflect the light reflected by the object (W) onto the second sensor array (C4) positioned outside the principal optical axis (y) and aligned onto the long-pass filter (C3).

8. The arrangement according to claim 1, wherein the optical measuring systems (D) for determining the diameter and (C) for determining the color of the object (W) are combined to form a third virtual measuring system (P) for determining a position of the object (W) inside the disk-shaped measurement volume (DCPv).

9. The arrangement according to claim 8, wherein the third measuring system (P) comprises a third illumination arrangement (P1) with two light sources (P1a, P1b), the first sensor array (DP4) and the first illumination arrangement (DP1) for triangulatory determination of the position of the object (W) inside the measurement volume (DCPv).

10. The arrangement according to claim 9, wherein the third illumination arrangement (P1) comprises a plurality of light sources each having different wavelength spectra and designed to illuminate the object (W) sequentially and thus sequentially project an image in the wavelength spectra of the light sources onto the second sensor array (C4).

11. The arrangement according to claim 1, wherein a measurement plane of the first sensor array (DP4) runs perpendicular to an x-y plane but intersects this at a small angle (a) to an x axis.

12. The arrangement according to claim 5, wherein the second sensor array (C4) is a multichromatic sensor and the light sources (C1a, C1b and C1c) of the second illumination arrangement (C1) are at least one of operated simultaneously or are replaced by a wide-band or multiband light source.

13. The arrangement according to claim 5, wherein the second sensor array (C4) is a multichromatic sensor and at least one of the light sources of the third illumination arrangement (P1) is replaced by a wide-band or multiband light source.

14. The arrangement according to claim 1, wherein the arrangement comprises a temperature sensor (T).

15. An installation for processing elongate objects (W) wherein the object (W) on an input side is provided by the arrangement for the automatic contactless detection of objects according to claim 1.

16. The arrangement according to claim 2, wherein the disk-shaped measurement volume (DCPv) is arranged centrally in a longitudinal direction.

17. The arrangement according to claim 16, wherein the disk-shaped measurement volume (DCPv) is coaxial with the guide device (4a, 4b).

18. The arrangement according to claim 5, wherein the second illumination arrangement (C1) comprises three light sources (C1a, C1b, C1c) which are placed close to one another.

* * * * *